United States Patent [19]

Goralski et al.

[11] 3,987,095
[45] Oct. 19, 1976

[54] N-SUBSTITUTED-1-(ARYLSULFINYL AND ARYLSULFONYL)METHANESULFONAMIDES

[75] Inventors: Christian T. Goralski; Thomas C. Klingler, both of Midland, Mich.

[73] Assignee: The Dow Chemical Company, Midland, Mich.

[22] Filed: Apr. 29, 1974

[21] Appl. No.: 465,035

Related U.S. Application Data

[62] Division of Ser. No. 337,866, March 5, 1973, Pat. No. 3,862,184.

[52] U.S. Cl. ............ 260/556 A; 260/247.1 R; 260/293.73; 260/556 AR; 424/248; 424/267; 424/321

[51] Int. Cl.² .......... C07C 143/75; C07C 143/79; A61K 31/18

[58] Field of Search ............ 260/556 AR, 556 A

[56] References Cited
UNITED STATES PATENTS

| | | | |
|---|---|---|---|
| 2,476,655 | 7/1949 | Fox et al. | 260/551 S X |
| 3,086,974 | 4/1963 | Schlor et al. | 260/556 A X |
| 3,412,149 | 11/1968 | Schlor et al. | 260/556 A |
| 3,654,359 | 4/1972 | Gosselink et al. | 260/551 S |
| 3,895,010 | 7/1975 | Goralski et al. | 260/556 A X |
| 3,927,090 | 12/1975 | Goralski et al. | 260/556 A |
| 3,946,007 | 3/1976 | Goralski et al. | 260/556 A X |

Primary Examiner—Floyd D. Higel
Assistant Examiner—Thomas A. Waltz
Attorney, Agent, or Firm—Theodore Post; C. Kenneth Bjork

[57] ABSTRACT

The compounds of the formula

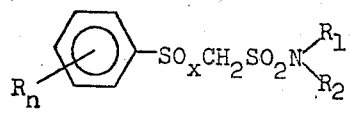

in which R independently is hydrogen, lower alkyl, lower alkoxy, halo or trifluoromethyl; $x$ is 1 to 2; $n$ is 1 to 3, and $R_1$ and $R_2$ independently are hydrogen, lower alkyl or phenyl and together with the nitrogen atom form a heterocycle which may contain an oxygen atom as a hetero atom. The compounds are prepared by reacting the corresponding N-substituted-1-(arylthio)methanesulfonamide with small, incremental amounts up to substantially equimolar of 30% hydrogen peroxide in glacial acetic acid at 65°–70° C., to obtain the sulfinyl compound, or substantially two equimolar proportions of 30% hydrogen peroxide in glacial acetic acid at reflux temperature to obtain the sulfonyl compound, and recovering the corresponding sulfinyl or sulfonyl product.

1 Claim, No Drawings

N-SUBSTITUTED-1-(ARYLSULFINYL AND ARYLSULFONYL)METHANESULFONAMIDES

This is a division of application Ser. No. 337,866 filed Mar. 5, 1973, now U.S. Pat. No. 3,862,184.

SUMMARY OF THE INVENTION

This invention concerns 1-(arylsulfinyl and arylsulfonyl)methanesulfonamides corresponding to the formula

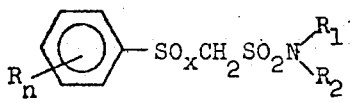

wherein R independently represents hydrogen, lower alkyl, lower alkoxy, halo or trifluoromethyl; $x$ represents an integer from 1 to 2; $n$ represents an integer from 1 to 3; and $R_1$ and $R_2$ independently represent hydrogen, lower alkyl or phenyl and together with the nitrogen atom form a heterocycle which may contain an oxygen atom as hetero atom. In the specification and claims, "lower alkyl" and "lower alkoxy" represent, respectively, a 1 to 4 carbon atom straight or branched chain alkyl group, such as, for example, methyl, ethyl, propyl, isopropyl, butyl, isobutyl, secondary butyl or tertiary butyl, or the corresponding alkoxy groups; and halo represents fluoro, chloro or bromo.

The compounds wherein $x$ represents 1 are prepared by adding small, incremental amounts up to substantially equimolar of 30% aqueous hydrogen peroxide to a 1-(arylthio)methanesulfonamide in the presence of glacial acetic acid as the solvent medium at about 65° to about 70° C. The 1-(arylsulfinyl)methanesulfonamide product is recovered from the reaction medium by allowing the acetic acid solution to cool to room temperature and allowing the product to crystallize out, or by pouring the latter onto ice and recrystallizing the precipitated solid product from ethanol. The compounds wherein $x$ is 2 are prepared by mixing a molar proportion of a 1-(arylthio)methanesulfonamide with substantially 2 molar proportions of aqueous 30% hydrogen peroxide in the presence of glacial acetic acid as reaction medium at about 20° to about 30° C. then at reflux temperature to form the 1-(arylsulfonyl)methanesulfonamide. The product is recovered by pouring the reaction medium onto ice and recrystallizing the product thereby obtained from ethanol.

DESCRIPTION OF SOME PREFERRED EMBODIMENTS

The following examples describe representative preparations and the best mode contemplated by the inventors of carrying out the invention. Temperature is given in Centigrade degrees. The compounds are identified by elemental analysis and nuclear magnetic resonance spectra (nmr).

EXAMPLE 1

N,N-Dimethyl-1-(phenylsulfonyl)methanesulfonamide

To a solution of 10 g. (0.043 mole) of N,N-dimethyl-1-(phenylthio)methanesulfonamide in 43 ml. of glacial acetic acid is added 15 ml. of 30% aqueous hydrogen peroxide. The mixture is stirred for 16 hours at 27° C. and then refluxed for one hour. The solution is poured onto ice and the precipitated solid recrystallized from ethanol to obtain 10.23 g. (90% yield) of fine white needles; m.p. 102°–103° C.

Anal. Calcd. for $C_9H_{13}NO_4S_2$: C, 41.05; H, 4.97; N, 5.32; S, 24.35. Found: C, 40.72; H, 5.14; N, 5.43; S, 24.20.

EXAMPLE 2

1-((3,4-Dichlorophenyl)sulfinyl)methanesulfonamide

To a solution of 0.50 g. (0.0018 mol.) of 1-((3,4-dichlorophenyl)thio)methanesulfonamide in 25 ml. of glacial acetic acid is added 0.10 g. of 30% hydrogen peroxide, and the reaction mixture is heated at 65° to 70° C. The progress of the reaction is followed by nuclear magnetic resonance spectroscopy, and over a period of 7 hours an additional 0.37 g. of 30% hydrogen peroxide is added in small incremental amounts. After the 7 hour reaction period, the acetic acid solution is allowed to cool, and the title compound separates as fluffy, white crystals. The crystals are filtered, washed with ether, and dried to give 0.37 g. of 1-((3,4-dichlorophenyl)sulfinyl)methanesulfonamide, m.p. 205°–207° C.

Anal. Calcd. for $C_7H_7Cl_2NO_3S_2$: C, 29.17; H, 2.45; Cl, 24.61; N, 4.86; S, 22.26. Found: C, 28.90; H, 2.52; Cl, 24.66; N, 4.96; S, 22.46.

EXAMPLE 3

Pursuant to procedures of Examples 1 and 2, the following 1-(arylsulfinyl- and arylsulfonyl)methanesulfonamides are prepared.

TABLE I

1-(ARYLSULFINYL AND ARYLSULFONYL)METHANESULFONAMIDES

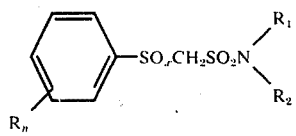

| | R | x | NR₁R₂ | Mp. ° C | Calculated C | Calculated H | Calculated N | Calculated S | Found C | Found H | Found N | Found S |
|---|---|---|---|---|---|---|---|---|---|---|---|---|
| (a) | 4-CH₃ | 2 | NH₂ | 179–181 | 38.54 | 4.45 | 5.62 | 25.72 | 38.19 | 4.38 | 5.55 | — |
| (b) | 4-CH₃ | 1 | NH₂ | 215–217 | 41.18 | 4.75 | 6.00 | 27.49 | 41.30 | 4.77 | 6.01 | 27.70 |
| (c) | 4-Br | 2 | NH₂ | 162–165" | — | — | — | — | — | — | — | — |
| (d) | 3,4-Cl₂" | 2 | NH₂ | 179–181 | 27.64 | 2.32 | 4.60 | 21.08 | 27.71 | 2.33 | 4.49 | 21.31 |
| (e) | 2,4,5-Cl₃" | 2 | NH₂ | 218–220 | 24.83 | 1.78 | 4.13 | 18.94 | 25.00 | 1.93 | 4.20 | 19.50 |
| (f) | 4-CH₃O | 2 | N(CH₃)₂ | 110–112 | 40.94 | 5.15 | 4.77 | 21.86 | 41.10 | 5.09 | 4.75 | 22.00 |

TABLE I-continued

1-(ARYLSULFINYL AND ARYLSULFONYL)METHANESULFONAMIDES

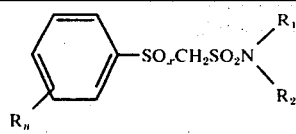

| | R | x | NR₁R₂ | Mp. °C | Calculated C | H | N | S | Found C | H | N | S |
|---|---|---|---|---|---|---|---|---|---|---|---|---|
| (g) | H | 2 | N⌒O (morpholino) | 154–155 | 43.26 | 4.95 | 4.58 | 21.00 | 43.24 | 5.16 | 4.63 | 20.90 |
| (h) | 4-Cl$^d$ | 2 | N⌒O (morpholino) | 128–130 | 38.88 | 4.15 | 4.12 | 18.87 | 39.19 | 4.12 | 4.23 | — |
| (i) | 4-(CH₃)₃C | 2 | N (piperidino) | 133–134.5 | 53.45 | 7.01 | 3.89 | 17.84 | 53.61 | 6.90 | 4.03 | 17.73 |
| (j) | H | 2 | N-CH(phenyl) piperidino | 125–127 | 56.97 | 5.58 | 3.69 | 16.90 | 56.69 | 5.52 | 3.60 | 17.01 |
| (k) | H | 2 | NH-phenyl | 151–153 | 50.14 | 4.21 | 4.50 | 20.60 | 50.01 | 4.15 | 4.43 | — |

$^a$Crude sample which was not analyzed.
$^b$Chlorine analysis. Calculated for C₇H₇Cl₂NO₄S₂: Cl, 23.31. Found: Cl, 23.10.
$^c$Chlorine analysis. Calculated for C₇H₆Cl₃NO₄S₂: Cl, 31.41. Found: Cl, 31.10. Chlorine analysis. Calculated for C₁₁H₁₄ClNO₅S₂: Cl, 10.43. Found: Cl, 10.25

The compounds of this invention are useful as intermediates for the preparation of the corresponding dihalomethane analogs, $$R_n-\bigcirc-SO_x-CY_2SO_2NR_1R_2,$$

wherein Y is chlorine or bromine and R, R₁, R₂, x and n have the meaning previously given. Thus, 1,1-dibromo-N,N-dimethyl-1-(phenylsulfonyl)methanesulfonamide is prepared from the compound of Example 1 by mixing the latter with aqueous sodium hypobromite in excess with stirring, filtering off the 1,1-dibromo product and recrystallizing the latter from ethanol. Similarly, 1,1-dibromo-1-((p-bromophenyl)sulfonyl)-methanesulfonamide is prepared by from the compound of Example 3(c) by reacting the latter with aqueous sodium hypobromite in excess and recrystallizing the resulting precipitate from a mixture of chloroform, methanol and hexane.

1,1-Dibromo-N,N-dimethyl-1-(phenylsulfinyl)methanesulfonamide is prepared by treatment of N,N-dimethyl-1-(phenylsulfinyl)methanesulfonamide with aqueous sodium hypobromite.

The dihalomethane analogs so prepared are useful as antimicrobials for the control of bacteria, fungi and yeasts such as S. aureus, C. albicans, E. coli, P. aeruginosa, S. typhosa, M. phlei, T. mentagrophytes, B. subtilis, C. pelliculosa, A. aerogenes, P. pullilans, A. terreus and R. nigricans. This is not to suggest that such dihalo analogs are equally effective against the same organisms or at the same concentrations.

What is claimed is:
1. The compound 1-(phenylsulfonyl)methanesulfonanilide.

* * * * *